United States Patent [19]
Berger et al.

[11] Patent Number: 4,843,018
[45] Date of Patent: Jun. 27, 1989

[54] PROCESS FOR THE QUANTATIVE DETERMINATION OF FREE THYROXINE

[75] Inventors: Johann Berger; Helmut Jering, both of Tutzing, Fed. Rep. of Germany

[73] Assignee: Boehringer Mannheim GmbH, Mannheim, Fed. Rep. of Germany

[21] Appl. No.: 797,634

[22] Filed: Nov. 13, 1985

[30] Foreign Application Priority Data

Nov. 23, 1984 [DE] Fed. Rep. of Germany ....... 3442817

[51] Int. Cl.$^4$ ........................................... G01N 33/543
[52] U.S. Cl. .................................... 436/500; 436/518; 436/807
[58] Field of Search ................ 436/500, 518, 530, 807

[56] References Cited

U.S. PATENT DOCUMENTS

| 4,017,597 | 4/1977 | Reynolds | 436/531 |
| 4,067,959 | 1/1978 | Bolz | 436/518 |
| 4,292,296 | 9/1981 | Parsons, Jr. | 424/1 |
| 4,366,143 | 12/1982 | Midgley et al. | 436/501 |
| 4,410,633 | 10/1983 | Hertl et al. | 436/500 |
| 4,477,576 | 10/1984 | Deutsch et al. | 436/518 |

OTHER PUBLICATIONS

C. N. Hales et al, *Meth. Enzymol.*, 70, 334–355, 1980.
*Coat-A-Count Free Thyroxine*, Diagnostic Products Corporation, 1983.

*Primary Examiner*—Sam Rosen
*Assistant Examiner*—David A. Saunders
*Attorney, Agent, or Firm*—Felfe & Lynch

[57] ABSTRACT

The present invention provides a process for the quantitative determination of free thyroxine ($FT_4$) in plasma, serum or whole blood by immunological methods, wherein the sample is incubated for at most 10 minutes with a 10 to 2000 fold insufficiency of labelled anti-$T_4$ antibodies, referred to the molar amount of total $T_4$ in the sample, then immediately brought together with immobilized excess $T_4$, again incubated, the phases separated and the label measured in one of the phases.

6 Claims, No Drawings

PROCESS FOR THE QUANTATIVE DETERMINATION OF FREE THYROXINE

The present invention is concerned with a process for the quantitative determination of free thyroxine in plasma, serum and whole blood.

According to present knowledge, thyrozine ($T_4$) is bound to an extent of about 80% to TBG (thyroxine-binding globulin), to an extent of about 15% to TBPA (thyroxine binding pre-albumin) and to an extent of about 5% to albumin. As binding constants, there are given about $2 \times 10^{10}$ 1/mole for TBG, about $10^6$ to $10^8$ for TBPA and $10^5$ to $10^6$ for albumin. A very small amount of the $T_4$ is "free", i.e. is present in a form not bound to protein and is called "$FT_4$". $FT_4$ appears to be present in an amount of about 0.01 to 0.03%, referred to the total amount of $T_4$. In the case of a $T_4$ normal range of 100 nmole/l., that corresponds to a concentration of about 10 pg./ml. or of 15 pmole/l. in the normal range. It is assumed that only $FT_4$ is actually physiologically effective since it can pass the cell membrane wall in contradistinction to protein-bound $T_4$. $FT_4$ is then in equilibrium with the protein-bound $T_4$ in the blood which, in the first place, serves as buffer for the regulation of the $FT_4$ level.

Therefore, the concentration of $FT_4$ reflects the functional state of the thyroid independently of changes in the concentration or saturation of thyroxin-binding protein and is, consequently, of clinical importance.

The recognised reference method for the determination of $FT_4$ depends upon an equilibrium dialysis of serum which has been enriched with radio-actively-labelled $T_4$ or upon a radioimmune assay of the dialysate without previous enrichment with radioactively-labelled $T_4$ (see J. Clin. Immunoassay, 7, 192–205/1984).

This method is regarded as being dependable but cannot be used for routine determinations because of the very great time requirement (12 hours incubation and 18 hours dialysis).

It has also already been suggested to carry out an extraction with anti-$T_4$ antibodies or to determine $FT_4$ by calculation by multiplication of total $T_4$ with the so-called $T_3$ uptake or to calculate by total $T_4$ multiplied by 1/TBG with the assumption that the values so obtained correlate under most circumstances with the concentration of $FT_4$ (see J. Clin. Immunoassay, 7, 192–205/1984). Another method depends upon the use of a $T_4$-analogous tracer which is certainly to be bound by anti-$T_4$ antibodies but not by the serum proteins (see U.S. Pat. No. 4,366,143). However, the correctness and affirmative force of this process is doubtful (see Clin. Chemistry, 30, 491–493/1984; J. of Clin. Immunoassay, 7, 192–205/1984).

Therefore, it is an object of the present invention to provide a process of high exactitude which is simple to carry out and which is also especially suitable for automation.

Thus, according to the present invention, there is provided a process for the quantitative determination of free thyroxine ($FT_4$) in plasma, serum or whole blood by immunological methods, wherein the sample is incubated for a short time, preferably no more than 10 minutes with an insufficiency of labelled anti-$T_4$ antibodies referred to the molar amount of total $T_4$ in the sample, then immediately brought together with excess immobilised $T_4$, again incubated, the phases separated and the labelled measured in one of the phases.

By means of the combination of a very large insufficiency of labelled anti-$T_4$ antibodies and of a very short incubation time up to contacting with excess immobilised $R_4$, it is, surprisingly, possible to determine the extremely small amounts of $FT_4$ very accurately.

The period of incubation of the sample with the labelled anti-$T_4$ antibodies present in very great insufficiency is to be kept as short as possible and is, therefore, preferably carried out for 1 to 5 minutes. The process according to the present invention permits still shorter incubation times and a period of incubation in the range of 10 to 30 seconds can still be used for the process according to the present.

The insufficiency of labelled anti-$T_4$ antibodies, which is referred to the molar amount of total $T_4$ in the sample, preferably corresponds to the percentage amount of $FT_4$, referred to the total $T_4$. A 10 to 2000 fold insufficiency has proved to be especially suitable and preferably a 50 to 2000 fold insufficiency. However, the labelled anti-$T_4$ antibodies can also be used in an insufficiency or excess with regard to $FT_4$. In the case of an excess, it is recommended to work in the lower time range for the first incubation but, in the case of an insufficiency, the upper time limit can also be utilised.

The second incubation with excess immobilised $T_4$ should not be less than 1 minute. As a rule, 1 to 10 minutes are well suited but longer incubation times can admittedly be used but do not provide any advantage. In practice, an incubation of 4 to 6 minutes gives very good results. These incubation times are also well suited for carrying out the process in automatic analysers.

As antibodies, there are preferably used those, the affinity of which is the same as or lower than the affinity of $T_4$ toward the binding protein (TBG). Especially preferably,, there are used anti-$T_4$ antibodies with an affinity constant of $10^{10}$ 1/mole or less.

The anti-$T_4$ antibody in the immunological test can be labelled in known manner. Suitable labels can take place, for example, by covalent linking with a readily determinable enzyme, such as peroxidase, $\beta$-galactosidase or the like, by optically determinable ligands, such as fluorescent, phosphorescent and similar substances or by radioactive labels. These methods are very well known and do not here require a detailed explanation. An enzyme labelling is preferred.

As already mentioned, the immobilised $T_4$ present in solid phase must be present in excess. An excess is preferred which corresponds to about the 10 to 5000 fold amount, referred to the molar amount of marked anti-$T_4$ antibodies used, and especially preferably to a 100 to 1000 fold excess. Substantially greater amounts can be used but they do not improve the result and increase the cost. Going below down to an excess of about 5 fold is also possible but it is then recommended to increase the period of time of the second incubation.

The immobilisation of the $T_4$ can take place, for example, according to the usual methods of immobilisation, of which covalent binding to a reactive matrix, coupling via difunctional bridge builders, surface adsorption and surface cross-linking with cross-linking agents, such as gluteraldehyde, and immunological precipitation are to be mentioned.

As carriers, there can be used all inert solid carrier materials which make possible a sufficient binding of $T_4$ and, on the other hand, do not exert any harmful side actions on the reaction. However, the shape and material of the carrier are less important. Preferably, there are used planar carriers, such as a pad, foamed material films and the like, paper being especially preferred.

The period of incubation of the first step of the process according to the present invention corresponds to the time between the mixing of the sample with the labelled anti-$T_4$ antibodies and the bringing together of the mixture thereby obtained with the immobilised $T_4$. The second incubation begins with the ending of the first incubation and ends with the phase separation. For the maintenance of the given short incubation times, there can be used the methods well known to the expert, for example mixing of sample and antibody solution, incubation and application of the mixture to a column with immobilised $T_4$ or transfer to a test tube with wall-bound $T_4$. The separation and transfer preferably take place by centrifuging, for which purpose the process and device described in European Patent Specification No. 0,073,513 are especially suitable.

By means of the present invention, the determination of $FT_4$ can be carried out in the simplest manner in a very short time with great exactitude and thus a routine process is provided which can, in particular, be carried out with automatic analysers, which permits the diagnostic importance of $Ft_4$ also to be fully utilised in practice.

The following Examples are given for the purpose of illustrating the present invention:

EXAMPLE 1

For carrying out the process, there was used the method and the insert elements described in FIGS. 1a and 1b for a centrifugal automatic analyser described in European Patent Specification No. 0,073,513. This insert element contains seven chambers connected with one another, each of which contains a fleece and each of which is successively passed by liquid under the influence of centrifugal force.

The following fleeces and impregnation solutions were used for the fleece:
Fleece 1: filter paper
impregnation solution: 3 o/oo wetting agent (Tween 20).
Fleece 2: filter paper
impregnation solution:
  100 mmole sodium phosphate buffer, pH 7.2
  5 mmole EDTA
  1% bovine serum albumin
  0.75 o/oo wetting agent (Tween 20)
Fleece 3:
  paper used: filter paper
  impregnation solution: anti-$T_4$ antibodies from sheep, labelled with $\beta$-galactosidase, 100 mU/ml. activity determined wtih o-nitrophenylgalactoside as substrate
  1% bovine serum albumin
  4 mMole magnesium aspartate
  50 mmole Hepes buffer, pH 7.2.
Fleece 4: filter paper activated with cyanogen bromide and reacted with $T_4$
Fleece 5:
  paper: filter paper
  impregnation solution: 15 mM chlorophenol red galactoside (CPRG) (prepared according to Federal Republic of Germany Patent Specification No. 33 45 748).

The chambers of the insert element were furnished as follows:

chamber I: 1 fleece 1
chamber II: 1 fleece 2
chamber III: 1 fleece 3
chamber V: 2 fleece 4
chamber VI: 1 fleece 5.

The serum used as sample solution was diluted 1:15 with 0.9% aqueous sodium chloride solution. 60 $\mu$l. of the solution so obtained were pipetted into the sample introduction chamber of the insert element and then the following centrifuging programme was carried out:
25 seconds, 250 rpm, dissolving of detergent, buffer and conjugate; start of the first incubation
20 seconds, 2000 rpm
300 seconds, 600 rpm incubation of sample and anti-$T_4$ antibody conjugate
300 seconds, 0 rpm, incubation with carrier-fixed $T_4$
15 seconds, 2000 rpm, ending of the second incubation
15 seconds, 0 rpm
5 seconds, 100 rpm, transport of the liquid to the cuvette
50 seconds, 720 rpm, measurement at 578 nm.

With the above-described centrifuging programme, the wetting agent is first dissolved from fleece 1 for easing the liquid transport. Subsequently, the buffer and conjugate fleece are soaked and the components present thereon are dissolved out. After incubation for 300 seconds in the first valve chamber, in which $FT_4$ binds with the anti-$T_4$ antibody-enzyme conjugate, the unreacted part of conjugate is bound to immobilised $T_4$ in the next 300 seconds step. After centrifuging off of a fleece on which is present the substrate (CPRG) and which is thereby dissolved off, the liquid passes into the cuvette where the optical density increase is followed for 50 seconds. The evaluation takes place by means of a calibration curve.

EXAMPLE 2

Test principle:
Microtitre (trademark of Dynatech Laboratories) plates or synthetic resin test tubes are coated with $T_4$-polyhapten (coupling of $T_4$ to bovine serum albumin, prepared according to Federal Republic of Germany Patent Specification No. 26 31 656). In a first reaction, the sample is incubated in an inert vessel with antibody-enzyme conjugate for 1 to 5 minutes. Subsequently, this solution is pipetted into the microtitre plates or synthetic resin test tubes. After 5 minutes, the solution is removed and the enzyme activity determined either of the solid phase or of the supernatant removed.

Coating buffer: 0.2 mole sodium bicarbonate (pH 9.5)+0.01% bovine serum albumin.
Coating with 200 $\mu$l. coating buffer+100 $\mu$g./ml. $T_4$-polyhapten.

After incubation for 10 minutes at ambient temperature, sucking off is carried out and again coated for 10 minutes with 50 mmole sodium phosphate (pH 7.2), 100 mmol sodium chloride and 1% bovine serum albumin and again sucked off.

20 $\mu$l. of sample are mixed with 200 $\mu$l. of buffer (50 mmole sodium phosphate (pH 7.2), 100 mmole sodium chloride and 1% bovine serum albumin) and 80 $\mu$l. of buffer+10 mU of conjugate and incubated at ambient temperature for 5 minutes. Subsequently, 200 $\mu$l. are pipetted into the microtitre plates of synthetic resin test tubes and, after incubating for 5 minutes at ambient temperature, 200 $\mu$l. are sucked off, washed with 200 $\mu$l. of buffer and, after again sucking off, mixed with 800 $\mu$l. of substrate (5 mmole/liter CPRG, 50 mmole Hepes (pH 7.2)). The increase of the absorption is followed for 5 minutes at $\lambda=578$ nm. The increase is the measurement signal and the concentration determination is carried out via a calibration curve.

It will be understood that the specification and examples are illustrative but not limitative of the present invention and that other embodiments within the spirit and scope of the invention will suggest themselves to those skilled in the art.

We claim:

1. Process for quantitative determination of free thyroxin (FT4) in a sample of plasma, serum or whole blood comprising incubating the sample with a 10 to 2000 fold insufficiency of labelled anti-T4 antibodies, referred to the molar amount of total T4 in the sample in a first incubation step for from 1 to 5 minutes, incubating said sample and anti-T4 antibodies with immobilized T4 which is in excess as compared to said antibodies in a second incubation step for from 1 to 5 minutes, separating the phases and measuring the label in one of the phases as a measure of free thyroxin in the sample.

2. Process according to claim 1, wherein an anti-thyroxin antibody is used which has an affinity constant of $10^{10}$ 1/mole or less.

3. Process according to claim 1, wherein there is used labelled anti-thyroxin antibody which has been dissolvably impregnated or lyophilized in dry form on a solid carrier material.

4. Process according to claim 3, wherein the labelled anti-thyroxin antibody is provided on a carrier, the sample is applied to the carrier and, after the first incubation, said sample is centrifuged and contacted to a second carrier which contains immobilized thyroxin.

5. Process of claim 1, wherein said immobilized thyroxin (T4) is present in an amount from about 10 to about 5000 times the molar amount of anti-thyroxin antibodies used.

6. Process of claim 1, wherein said immobilized thyroxin (T4) is present in an amount from about 100 to about 1000 times the molar amount of anti-thyroxin antibodies used.

* * * * *